United States Patent
Huhn et al.

(10) Patent No.: US 7,067,086 B2
(45) Date of Patent: Jun. 27, 2006

(54) MICROFLUIDIC ACCUMULATING AND PROPORTIONING COMPONENT

(75) Inventors: Rüdiger Huhn, Lübeck (DE); Roger Blum, Hamburg (DE); Dietmar Sander, Hamburg (DE); Lutz Timmann, Bad Bramstedt (DE)

(73) Assignee: Eppendorf AG, Hamburg (DE)

( * ) Notice: Subject to any disclaimer, the term of this patent is extended or adjusted under 35 U.S.C. 154(b) by 654 days.

(21) Appl. No.: 10/143,400

(22) Filed: May 9, 2002

(65) Prior Publication Data

US 2002/0168298 A1 Nov. 14, 2002

(30) Foreign Application Priority Data

May 12, 2001 (DE) .................................. 101 23 259

(51) Int. Cl.
*B01L 3/02* (2006.01)
(52) U.S. Cl. .................. 422/100; 422/72; 422/102
(58) Field of Classification Search ................ 422/100, 422/102, 104, 72
See application file for complete search history.

(56) References Cited

U.S. PATENT DOCUMENTS

| 4,618,476 | A | * | 10/1986 | Columbus .................. 422/100 |
| 5,356,034 | A | * | 10/1994 | Schlumberger .............. 222/61 |
| 5,916,522 | A | * | 6/1999 | Boyd et al. .................. 422/58 |
| 6,063,589 | A | * | 5/2000 | Kellogg et al. ............... 435/24 |
| 6,184,040 | B1 | * | 2/2001 | Polizzotto et al. ............ 436/43 |
| 2002/0011276 | A1 | * | 1/2002 | Sander ....................... 141/59 |
| 2004/0053322 | A1 | * | 3/2004 | McDevitt et al. ........... 435/7.1 |

* cited by examiner

*Primary Examiner*—Jill Warden
(74) *Attorney, Agent, or Firm*—Abelman, Frayne & Schwab

(57) ABSTRACT

A microfluidic accumulating and proportioning component, including:
- a reservoir including an aeration port and an outlet disposed below for a liquid,
- capillary cavities in the reservoir,
- a displacement chamber which is disposed at least partly at the same level as the reservoir, with an inlet disposed above and a proportioning outlet disposed below for a liquid, and
- a rising capillary channel connecting the outlet of the reservoir to the inlet of the displacement chamber.

8 Claims, 9 Drawing Sheets

MICROFLUIDIC ACCUMULATING AND PROPORTIONING COMPONENT

BACKGROUND OF THE INVENTION

1. Field of the Invention

This invention relates to a microfluidic accumulating and proportioning component.

2. Description of the Prior Art

Microfluidic accumulating and proportioning components in the sense of this application serve for accumulating and/or and proportioning liquids. Such microfluidic components feature microstructures such as capillary channels or ports having characteristic dimensions which, for instance, include the hydraulic diameter of the channels in the range from 5 µm to 1,500 m (preferably from 10 µm to 500 µm) in one dimension. In particular, microfluidic proportioning components may have proportioning volumes in the nanoliter range and microliter range. They may be specifically manufactured from semiconductors and/or plastics and/or glass and/or ceramics and/or metals where appropriate manufacturing techniques of the micro-system technology or microstructuring may be employed, e.g. lithography and etching processes (for semiconductors) or Liga processes (for metals, plastics, and ceramics).

WO 99/10099 describes various microproportioning systems which are intended for proportioning volumes in the range of a few nanoliter up to some microliters and use an open-jet proportioner and/or a micro-diaphragm pump. One of these microproportioning systems has a proportioning and reagent unit. The unit has a reservoir with a filter for pressure compensation with the environment and a micro-diaphragm pump and/or open-jet proportioner connected thereto via a line. It further has an outwardly projecting delivery tube with a proportioning outlet. In addition, there is a proportioning control for the micro-diaphragm pump. The proportioning and reagent unit is adapted to be inserted into a receptacle in the base area of a casing so as to make the delivery tube axially protrude beyond the base area. The proportioning control is connected to an optical sensor fixedly disposed in the casing base which is associated with the delivery tube of the insertable proportioning and reagent unit.

This proportioning system is prepared for operation by inserting a proportioning and reagent unit prefilled with a reagent (e.g. an enzyme) into the receptacle of the casing. In the first proportioning step, the micro-diaphragm pump draws off liquid from the reservoir until the sensor detects the meniscus and, thus, reaches a defined zero position. From this point onwards, the volume to be proportioned is controlled via the known stroke volume of the micro-diaphragm pump. Once the proportioning and reagent unit is empty it is exchanged against a new, prefilled unit.

This document further discloses a microproportioning system with a reservoir having a capillary compensation system, an open-jet proportioner the inlet of which is connected to the capillary compensation system, a proportioning outlet connected to the outlet of the open-jet proportioner and a proportioning control which is in an operative communication with the open-jet proportioner. The capillary compensation system serves for the accumulating and capillary conveyance of the liquid into the open-jet proportioner from the reservoir. Apart from this, it may be used to balance variations of the ambient conditions such as air pressure and temperature and to compensate the liquid volume consumed by the open-jet proportioner. The capillary compensation system prevents the formation of bubbles which could appear in the accumulated liquid volume during an acceleration, e.g. during a fall of the reservoir, and could interfere with the proportioning process. The capillary compensation system may be aerated in at least one point remote from a connection with the open-jet proportioner in order that liquid which flows out be made up for by air which flows in. At the same time, the capillary forces will then prevent leakage from the reservoir. The previously described microproportioning system may also have such a capillary compensation system.

However, a leakage of liquid or formation of bubbles with concomitant liquid losses and faulty proportionings may still occur in the previously described microproportioning system.

Therefore, it is the object of the invention to provide a microfluidic accumulating and/or proportioning component in which the controlled storage and delivery of liquid is further improved.

SUMMARY OF THE INVENTION

The object is attained by various solutions related to microfluidic accumulating and/or proportioning components.

In the various solutions, the indications "at bottom", "at top", "at the same level" or "at the same height" refer to an orientation of the microfluidic accumulating and/or proportioning component which has its proportioning outlet directed perpendicularly downwards during proportioning, which corresponds to a frequent orientation of the component in causing liquid to exit from the proportioning outlet, which can be performed by a discharge of liquid or in an open jet. Generally, the component may be randomly oriented when in use, particularly for delivery in an open jet.

In the various solutions, the indications "capillary cavities", "capillary rising channel", "capillary filling channel", "capillary channels" or "capillary connections", hereinafter referred to as "capillary structures", further refer to cavities (e.g. channels or pores), channels (e.g. in the shape of gaps, slots or tubes) or connections (e.g. channels or pores) in which wetting liquids rise or flow in one direction or are retained by capillary forces and in which, if filled with wetting liquids, an increased capillary pressure makes itself felt at the interface with air or some other gas. The extent of such capillary effects can be acted on, first and foremost, by the dimensions of the capillary structures, but also by their materials or their surface finish. For simplicity, the propension of the capillary structures to having such capillary effects will be hereinafter referred to as "capillarity".

The first solution relates to a microfluidic accumulating and proportioning component, comprising:
- a reservoir including an aeration port and an outlet disposed below for a liquid,
- capillary cavities in the reservoir,
- a displacement chamber which is disposed at least partly at the same level as the reservoir, with an inlet disposed above and a proportioning outlet disposed below for a liquid, and
- a rising capillary channel connecting the outlet of the reservoir to the inlet of the displacement chamber.

The capillary cavities in the reservoir already cause a reduction of the pressure the liquid has in the proportioning outlet. The pressure of the liquid is additionally reduced in the proportioning outlet because the reservoir and the displacement chamber are partially disposed at the same level since this diminishes the hydrostatic pressure of the liquid. It is preferred that the capillary cavities and the levels of the reservoir and displacement chamber are designed in such a way that the capillary pressure of the liquid in the reservoir at least corresponds to the hydrostatic pressure of the liquid in the proportioning outlet. The overall pressure of the liquid in the proportioning outlet will then maximally correspond to the ambient pressure such that liquid will not leak out by itself.

The reservoir and/or the displacement chamber preferably extend over a certain height each. The invention includes the fact that the reservoir and/or the displacement chamber are disposed at the same level only in partial regions of their entire height. Preferably, the reservoir and/or the displacement chamber are substantially disposed at the same level along their entire height.

If the component is vertically oriented the liquid rises into the rising channel from the reservoir according to the principle of communicating tubes. Whatever the filling level of the reservoir might be, the supply of liquid into the displacement chamber from the reservoir is ensured even if the component is vertically oriented as the liquid rises in the capillary rising channel because of the capillary effect. The transfer of liquid into the displacement chamber from the reservoir through the rising channel functions whatever the orientation of the component is so that it may be operated at a random orientation. Further, the capillary cavities and the capillary rising channel provide for the reservoir, the rising channel, and the displacement chamber to be completely filled with nonbubbling liquid and counteract the formation of bubbles resulting from bumps against the component.

According to another aspect, a connection channel is disposed between the rising channel and the inlet of the displacement chamber with which a filling level sensor is associated. The filling level sensor can serve for monitoring the complete filling of the displacement chamber with liquid in order to avoid faulty pro-portionings. The filling level sensor can particularly be an optical sensor which detects bubbles and/or liquid or the phase boundary therebetween.

According to another aspect, the rising capillary channel is laterally connected to the reservoir via a capillary gap with the capillary gap being designed so as to cause a liquid to flow substantially from the outlet of the reservoir into the displacement chamber through the capillary rising channel in the proportioning mode and, if the component is disposed in a centrifugal field directed counter to the direction of flow in the rising channel in the proportioning mode, to cause a liquid to flow from the displacement chamber and the rising channel into the reservoir through the gap.

This makes it possible to remove bubbles from the liquid-carrying regions of the component, specifically from the displacement chamber and the rising channel. To this end, the all of the liquid from the displacement chamber, the rising channel, and the reservoir may be collected at the top of the reservoir in order to fill the rising channel, the reservoir, and the displacement chamber again subsequently. This is problematic due to the fact that the reservoir and the displacement chamber are at the same level at least in part and the outlet disposed at the bottom of the reservoir is connected to the inlet disposed at the top of the displacement chamber. This basically counteracts a collection of the entire liquid from the system by centrifuging. The problem is remedied by fluidically linking the rising channel and, thus, the displacement chamber to the reservoir through the lateral gap of increased capillarity. The increased capillary pressure of the liquid in the gap ensures that the rising channel, in the proportioning mode, acts like a laterally closed channel through which liquid virtually passes only into the inlet of the displacement chamber from the outlet of the reservoir.

When centrifuging is done the weighting forces acting on the liquid in the rising channel will increase such that the capillary pressure in the gap is no longer capable of preventing the liquid from exiting into the reservoir. Hence, when centrifuging is done the rising channel will act like a laterally open channel through the gap of which liquid is pressed into the reservoir from the displacement chamber and the rising channel. The rising channel and the capillary cavities of the reservoir are filled with non-bubbling liquid again by turning the component over subsequently. Moreover, the displacement chamber is refilled with non-bubbling liquid through the rising channel.

It is preferred that the gap opens at least partly into a region of the reservoir above the capillary cavities. In this region, when centrifuging is done liquid may exit from the rising capillary channel directly into the upper region of the reservoir in order to gather there in the same way as the liquid from the capillary cavities of the reservoir. Although an ambient pressure prevails in the upper region of the reservoir because of the aeration port the rising capillary channel is laterally sealed at top by the capillary pressure of the liquid in the gap against the reservoir when centrifuging is done. This is the case as long as the capillary pressure in the gap exceeds the negative pressure in an adjoining point in the rising capillary channel.

The negative pressure in the rising capillary channel, i.e. the difference between the pressure in the rising channel and the ambient pressure, is composed of a hydrostatic pressure proportion because of the height of the rising capillary channel, a pressure loss proportion because of the flow of the liquid in the rising capillary channel, and a capillary pressure proportion which relies on the oppositely acting capillarities of the capillary cavities of the reservoir and the rising capillary channel. The negative pressure in the rising capillary channel depends on the height of the point regarded in the rising channel.

As a result, the capillary pressure in the gap along the height of the gap may differ. Therefore, according to an advantageous aspect, the capillarity of the rising capillary channel increases from the outlet of the reservoir to the upper end of the rising capillary channel, preferably because the width of the gap diminishes from bottom to top. Since the negative pressure in the rising capillary channel also depends on the volume of the liquid an upper limit results for the volumetric flow in proportioning at which the capillary pressure in the gap laterally seals the rising channel.

According to an advantageous aspect, the component has a filling port at top that is connected to the reservoir. This makes it possible to fill the reservoir with liquid and, moreover, to completely empty the reservoir after centrifuging, e.g. to recover a liquid residue. The filling port may be closed durably or openably after the filling operation. Preferably, a capillary filling channel is disposed between the filling port and the rising channel. This makes it possible to initially wet the rising channel during filling and to fill the reservoir subsequently. This can avoid forming air inclusions in the liquid-carrying regions of the component. The filling channel may also have a lateral gap via which it can be filled.

According to an advantageous aspect, the reservoir and the displacement chamber are substantially disposed in parallel layers of at least one planar body, which is made possible by a very compact construction. According to another aspect, the rising channel is disposed in the same layer as the reservoir, and according to yet another aspect the connection duct is disposed in the same layer as the displacement chamber. The liquid may pass into the inlet of the displacement chamber and in the connection channel from the rising channel through a passage of the planar body that is oriented transversely to the parallel layers.

Preferably, the proportioning outlet is disposed in one end face and/or the filling port is disposed in the other end face of the at least one planar body.

According to another advantageous aspect, the component is set up by a plurality of superposed planar bodies. The superposed bodies may be connected to each other on the separating planes. According to another aspect, the component is set up by three superposed bodies. Preferably, the reservoir and/or the rising channel and/or the filling channel are disposed on one large-surface side of a planar basic body, the displacement chamber and/or the connection channel are disposed on the other large-surface side of the planar basic body, the transversely directed passage is disposed in the planar basic body in a transverse direction, the proportioning outlet is disposed in one end face and/or the filling port is disposed in the other end face of the planar basic body and the planar basic body is closed by a reservoir lid on the side of the reservoir and by a membrane lid on the side of the displacement chamber. According to another aspect, the reservoir lid partly contains the reservoir and/or the rising channel and/or the filling channel and/or the membrane lid partly contains/contain the displacement chamber and/or the connection duct.

The second solution relates to a microfluidic accumulating and/or proportioning component, comprising
a reservoir including an aeration port and an outlet for a liquid,
parallel capillary channels disposed in the reservoir and leading to the outlet of the reservoir and capillary connections directed transversely to the capillary channels and interconnecting adjacent capillary channels and connected to the outlet the capillarity of which exceeds that of the capillary channels.

In the capillary channels, the liquid is retained by capillary forces and does not leak out regardless of the position of the component. In the capillary connections, the liquid is retained by capillary forces which are even higher than those in the capillary channels because the capillary connections have a capillarity which exceeds that of the capillary channels. Furthermore, the capillary channels and capillary connections prevent the inclusion or the formation of bubbles in the reservoir. If bubble formation occurs notwithstanding this, e.g. due to a heavy bump, such formation preferably occurs in the capillary channels where capillarity is more intense. Accordingly, bubbles will only interrupt liquid columns in the capillary channels. Though, the liquid columns in the capillary connections are maintained. This ensures that liquid may be uninterruptedly withdrawn the outlet of the reservoir. It is easy for the bubbles to move up in the capillary channels, in which case the liquid displaced by the bubbles may escape into the capillary connections and the volumes taken by the bubbles may be filled up by liquid from the capillary connections. Hence, the reservoir favours an independent removal of gases.

The component may be designed exclusively as a reservoir for very varied applications, particularly in microfluidic systems (e.g. PCR, lab on chip, etc). It further may be a combined accumulating and proportioning component. To this end, according to an aspect, the outlet of the reservoir can have a connection to an inlet of a displacement chamber having a proportioning outlet for a liquid.

According to a preferred aspect, the capillary channels are defined by parallel lamellar strips and the capillary connections are defined by transversely directed linking gaps between the lamellar strips. The reservoir may be formed simply by assembling two planar bodies each of which supports lamellar strips which are flush with each other if the planar bodies are joined. Thus, for instance, the reservoir may be formed by means of two planar bodies from which lamellar strips protrude, and by means of a frame disposed therebetween.

According to a preferred aspect, the component has a planar basic body which has lamellar strips protruding on one side from the bottom of an indentation defining one part of the reservoir and has a reservoir lid disposed on this side of the basic body which has lamellar strips protruding from the bottom of an indentation defining a second part of the reservoir wherein the lamellar strips of the basic body and the lamellar strips of the reservoir lid are flush with each other and the transversely directed capillary connections are located between the lamellar strips of the basic body and the lamellar strips of the reservoir lid. This generally makes it possible to form the reservoir only from two planar bodies.

Preferably, the capillary connections are disposed in the separation plane between the basic body and the reservoir lid. In particular, the lamellar strips of one of the two bodies may be precisely extended up to the separation plane.

The component according to the second solution can be advantageously configured with the features of one or more of other solutions. The patent application incorporates all versions that are possible.

The third solution relates to a microfluidic accumulating and/or proportioning component, comprising:
a reservoir including an aeration port and an outlet for a liquid,
capillary channels disposed in the reservoir and leading to the outlet, and
shoulders at the ends of the capillary channels in which outlet ports of the outlet for a liquid are disposed that have a cross-section smaller than that of the capillary channels.

Also in this component, the liquid is retained by the capillary forces in the capillary channels regardless of the orientation of the component. In addition, the capillary channels counteract the formation of bubbles. If bubbles are formed notwithstanding that this solution prevents them from exiting, along with the liquid, from the exit of the reservoir and impairing the use of the liquid. For instance, this would be the case if the liquid was proportioned by means of a displacement chamber because if displacement exists the bubbles will collapse first so that either no liquid is delivered at all or the liquid volume delivered does not correspond to the proportioning volume desired. The retention of the gas bubbles in the capillary channels is due to the fact that these tend to be deposited on the walls of the capillary channels and not to be at a distance from the walls where the exit ports are located in the shoulder at the end of the capillary channels. Since it is rather rare that the gas bubbles are directly in front of the exit ports it is accordingly exceptional that they will get into the outlet.

The component may also be designed exclusively as a reservoir for very varied applications, particularly in microfluidic systems (e.g. PCR, lab on chip, etc). It further may be a combined accumulating and proportioning component. To this end, according to an aspect, the outlet can have a connection to an inlet of a displacement chamber having a proportioning outlet for a liquid.

According to another aspect, the capillary channels are parallel and/or straight-lined. This favours the removal of gases from the reservoir by the rise of the bubbles.

Preferably, the outlet ports are centrally oriented towards the capillary channels in order to promote the above-described effect of avoiding an entry of the bubbles in the exit ports.

The exit ports can be favourably formed in a separation plane between superposed, planar bodies. In an advantageous aspect, a planar basic body has one part of the reservoir on one side and a reservoir lid disposed on this side has another part of the reservoir and the shoulder has one part on the basic body and another part on the reservoir lid.

The component according to the third solution can be advantageously configured with the features of one or more of other solutions. The patent application incorporates all versions that are possible.

In all solutions, the reservoir has an aeration port which ensures pressure compensation between the air volume in the reservoir and the environment. Otherwise, if liquid exits, e.g. during proportioning, a negative pressure would arise in the reservoir and would counteract the exiting of the liquid. Furthermore, variations of the ambient conditions (pressure/temperature) would cause liquid to leak out or air to be drawn in through the proportioning outlet or the outlet of the reservoir. If the aeration port is wetted or is closed by liquid this would impair its function because pressure compensation would be impeded, as a result. Moreover, it would be possible for liquid to get out through the aeration port. Basically, this can be avoided by orienting the component in such a way that liquid from the reservoir does not enter the aeration port. If is further avoided because capillary cavities withhold the liquid in the reservoir so as to prevent it from getting into the aeration port. However, this cannot always completely prevent liquid from exiting through the aeration port.

The fourth solution relates to a microfluidic accumulating and/or proportioning component, comprising:

a reservoir including an aeration port and an outlet for a liquid, wherein the aeration port is disposed at a central location in the reservoir at a distance from reservoir limitation walls so that if the reservoir filled with a maximum admissible liquid volume is randomly oriented no liquid exits to the outside through the aeration port.

The maximum admissible liquid volume is smaller than the total volume of the reservoir. Its volume is such that although the reservoir is randomly oriented the liquid cannot enter the aeration port which is at a distance from the reservoir limitation walls.

This component may also be designed exclusively as a reservoir for very varied applications, particularly in microfluidic systems (e.g. PCR, lab on chip, etc). It further may be a combined accumulating and proportioning component. To this end, according to an aspect, the outlet of the reservoir can have a connection to the inlet of a displacement chamber having a proportioning outlet for a liquid.

The reservoir can further have a part including capillary cavities and a part free from capillary cavities in which the aeration port is disposed. The capillary cavities help in keeping the liquid away from the aeration port. The maximum admissible liquid volume is preferably limited to the volume for filling the capillary cavities. That part of the reservoir which is free from it can substantially have the same filling volume as the capillary cavities.

It is preferred that the aeration port has a sharp-edged bordering in order to avoid wetting the walls of the aeration port. A sharp-edged bordering prevents the liquid from creeping into the aeration port.

Preferably, this component may also be formed by a plurality of superposed, planar bodies. According to an advantageous aspect, the reservoir is at least partly formed as an indentation in one side of a planar basic body and a spigot protrudes from the bottom of the indentation the free end of which has disposed thereon the aeration port from which an aeration channel extends into the basic body through the spigot and extends to an outwardly leading mouth through the wall of the basic body. It is preferred that the aeration channel traverses the basic body and continues to pass on the other side thereof up to a front-end wall including the mouth. It is further preferred that a reservoir lid is disposed on the side of the basic body including the aeration port and which has an indentation defining another part of the reservoir. Preferably, the aeration port is then disposed in the separation plane of the basic body and the reservoir lid so that maximum distances can be maintained from the bottoms of the indentations in the basic body and the reservoir lid.

An open portion of the aeration channel on the other side of the basic body may be covered by another planar body which can be a diaphragm lid if a displacement chamber is formed on this side of the basic body.

It is further preferred that the aeration port has its mouth in a end face of the basic body in which also the proportioning outlet has its mouth. This allows to ensure a free access of air to the mouth. It further allows to jointly cover the mouth and the proportioning outlet.

The component according to the fourth solution can be advantageously configured with the features of one or more of other solutions. The patent application incorporates all versions that are possible.

The fifth solution relates to a microfluidic accumulating and proportioning component, comprising:

a reservoir including an aeration port, a displacement chamber connected to the reservoir including a proportioning outlet, a body comprising the reservoir and the displacement chamber, and an inscription flag connected to the body via a web.

The component may be attached to the body in its correct position so that an actuator may act on the displacement chamber, thus causing a proportioning operation. Since the body may have main dimensions ranging within a few millimeters and smaller and, if inserted into a proportioning device including an actuator cannot or can hardly be seen any longer any letters or marking on the body can no longer be perceived from outside. The inscription flag joined to the body via a web allows an arrangement outside the proportioning device which enables an identification of the component also in an application case. This is useful, for instance, to make it verifiable for a user with which liquid (e.g. a reagent or enzyme) the component is filled.

It is preferred that the body and the inscription flag are plate-shaped. According to another aspect, the body and the inscription flag are oriented perpendicularly to each other. The inscription flag, when in use, may closely bear against an outer surface of a proportioning device. Further, a slit can be located between said inscription flag and said body to receive a housing portion of a device accommodating the component.

The component according to the fifth solution can be advantageously configured with the features of one or more of other solutions. The patent application incorporates all versions that are possible.

The sixth solution relates to a microfluidic accumulating and proportioning component, comprising:

a reservoir including an aeration port, a displacement chamber connected to the reservoir including a proportioning outlet, a body in which the reservoir and the displacement chamber are formed and which has the proportioning outlet and/or a mouth of the aeration port in a end face, and a catch contour formed at the end face including the proportioning outlet.

Any contamination of the end face of the component including the proportioning outlet could cause a contamination of the liquid. Therefore, it is advantageous to close the end face with a closing cap both when the component is supported and when the component is employed in a proportioning device if no proportionings are made. Further, it is hardly possible to see with the naked eye to which place a proportioning is made. Therefore, an aim-taking aid is helpful which, for instance, can be constituted by a pointer body or an illuminated pointer. The catch contour at the component's end face allows to place the closing cap or aim-taking aid on the proportioning outlet simply and in a correct orientation. At the same time, a closing cap may cover an aeration port which is in the same end face.

According to a preferred aspect, the catch contour is of a dovetail shape. It includes a component which is connected to the closing cap or aim-taking aid.

The catch contour may also be employed for other purposes such as the positioning of a holder or carrier to hold or move away the component.

The component according to the sixth solution can be advantageously configured with the features of one or more of other solutions. The patent application incorporates all versions that are possible.

The configuration of the inlet and the proportioning outlet of the displacement chamber is the object of an optimization which is aimed at receiving a maximum liquid volume from the reservoir when the displacement chamber is expanded and avoiding an entry of air through the outlet. When the displacement chamber is compressed the whole liquid volume received should be delivered, if possible, from the proportioning outlet and as little air as possible should be forced back into the reservoir. It is preferred that the liquid is delivered from the proportioning outlet in an open jet. According to an advantageous aspect, the chamber can have an inlet with a throttle valve and/or a proportioning outlet with a nozzle.

According to another aspect which applies to all solutions, the component is releasably connected to a proportioning device which has an actuator acting on a wall of the displacement chamber of the component to shift the wall and to displace a liquid contained in the displacement chamber. The concerned wall of the displacement chamber is preferably a diaphragm lid.

Finally, according to another aspect which applies to all solutions, the component is releasably connected to a proportioning device which has a filling-level sensor to sense the filling level in the connection duct.

BRIEF DESCRIPTION OF THE DRAWINGS

The invention will now be explained in more detail with reference to the accompanying drawings of a preferred embodiment. In the drawings.

DETAILED DESCRIPTION OF THE PREFERRED EMBODIMENTS

Figure 1:
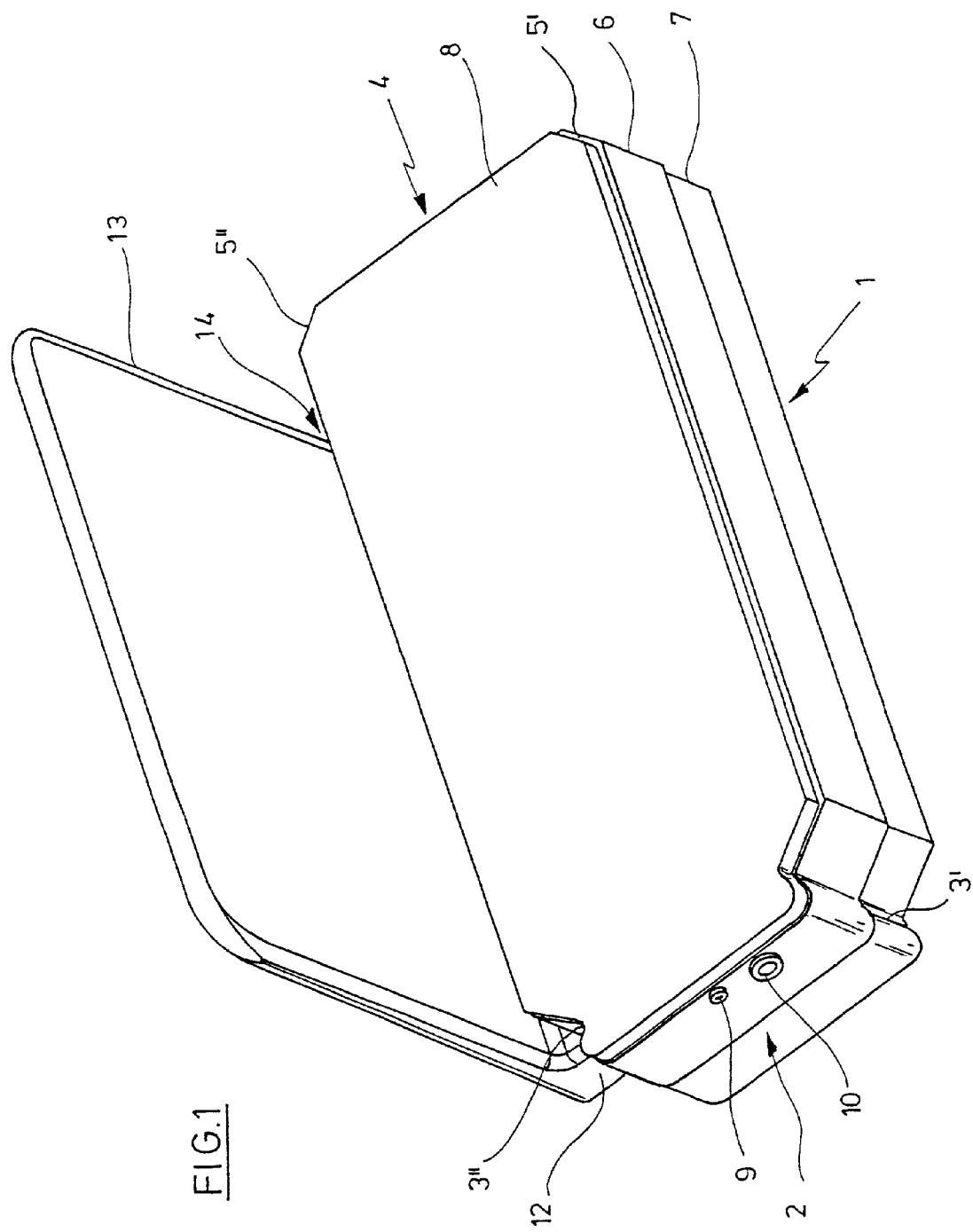
FIG. 1 shows the accumulating and proportioning component in a perspective view onto the diaphragm side.

Referring to FIG. 1, the microfluidic accumulating and proportioning component has a substantially planar body 1 which has a catch contour 3', 3" adjacent to one end face 2, which is of a dovetail shape if seen in a plan view, in the narrow sides and which is chamfered on the other end face 4 at 5', 5" towards the narrow sides.

The body 1 is formed from superposed plate-shaped bodies of a substantially complementary outer contour which comprise a basic body 6, a reservoir lid 6, and a diaphragm lid 8.

The body 1, more specifically the basic body 6, has a proportioning outlet 9 and a mouth 10 of an aeration duct in the end face 2.

Figure 2:
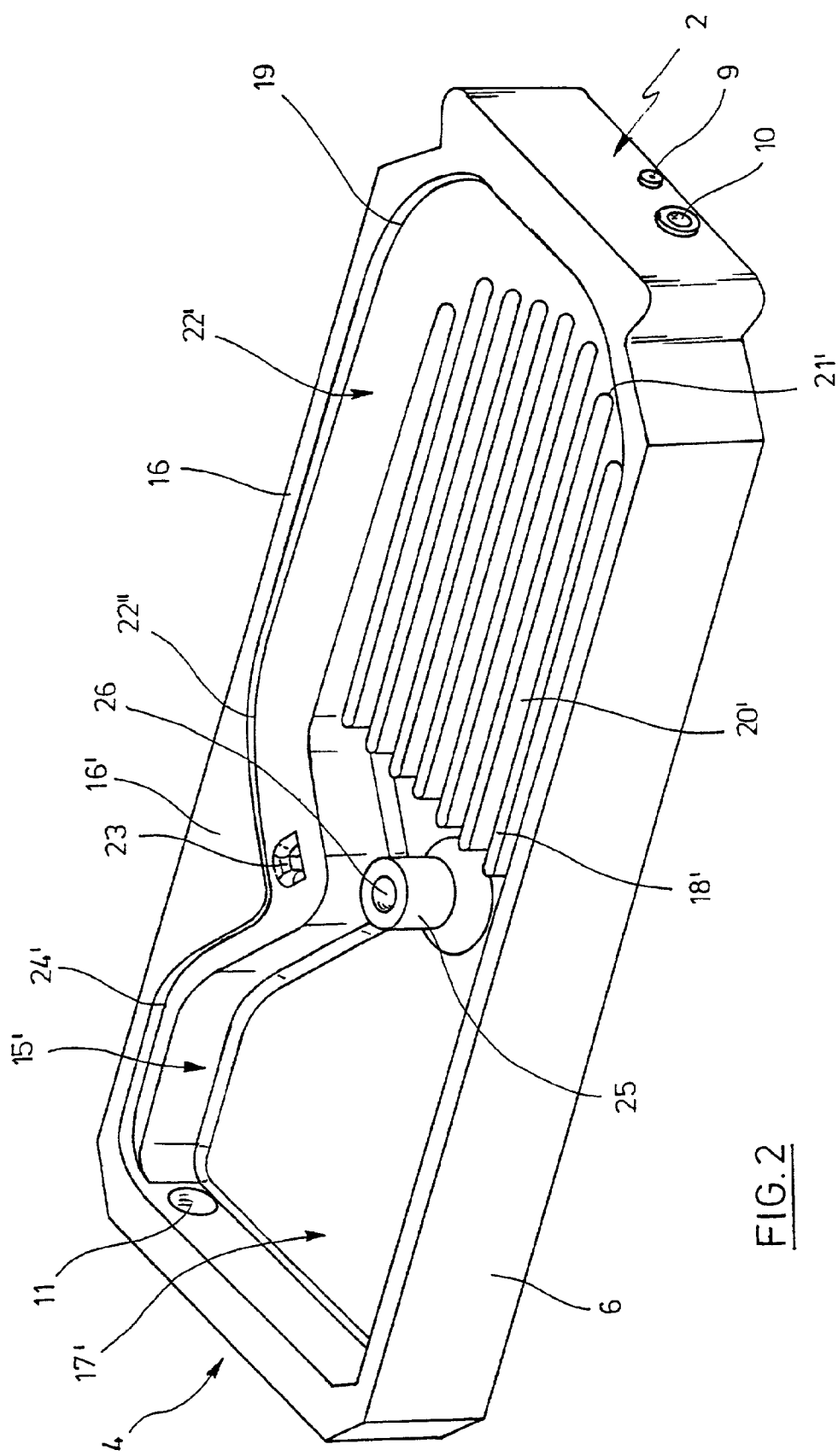
FIG. 2 shows the basic body of the same component in a perspective view onto the reservoir side.

Furthermore, the body 1, more specifically the basic body 6, has a filling port 11, which is shown in FIG. 2, in the end face 2.

Adjacent to the catch contour 3", the body 1 is connected, via a web 12, to an inscription flag 13 which is plate-shaped and is oriented perpendicularly to the body 1. A gap 14 is formed between the inscription flag 13 and the adjoining narrow side of the body 1.

Referring to FIG. 2, the basic body 6, in a large-surface side, has an indentation 15' which passes around the support surface 16. Lamellar strips 18' protrude from the bottom 17' of the indentation 15' and are oriented in the longitudinal direction of the basic body 6. The lamellar strips 18' start at a first step portion 19 which is formed in the indentation 15' next to the end face 2 including the proportioning outlet 9. The lamellar strips 18' end approximately at half the length of the basic body 6. Their upper edge is flush with the first step portion 19. Capillary channels 20' extend between the lamellar strips 18' and next to the outer lamellar strips 18'. These are limited by shoulders 21' towards the end face 2 and are open towards the end face 4.

At a narrow side of the basic body 6, starting from the first stepped portion 19, a second stepped portion 22' extends in the indentation 15' and its upper side (as referred to FIG. 1) is a limitation wall of a rising capillary channel 22.

Starting from the first step portion 19, the second step portion 22' slightly rises to the level of the support surface 16. The rise ends at a slightly S-shape curved third step portion 22" which partially is passed around an inwardly protruding region 16' of the support surface 16 and is at a constant distance from the support surface 16. The third step portion 22" also defines the rising capillary channel 22. A passage 23 oriented transversely to the basic body 6 has its mouth in the third step portion 22".

A fourth step portion 24' which starts from the third step portion 22" is extended up to the front face 4 the upper surface of which (as referred to FIG. 1) is a limitation wall of a filling channel 24. This limitation wall of the filling channel 24 also has a slight inclination with respect to the support surface 16 and has the least distance from the support surface 16 at the transition to the third step portion 22" and has the largest distance therefrom at the end face 4.

In the end face 4, the filling port 11 has its mouth in the indentation 15' directly next to the filling channel 24.

Figure 4:
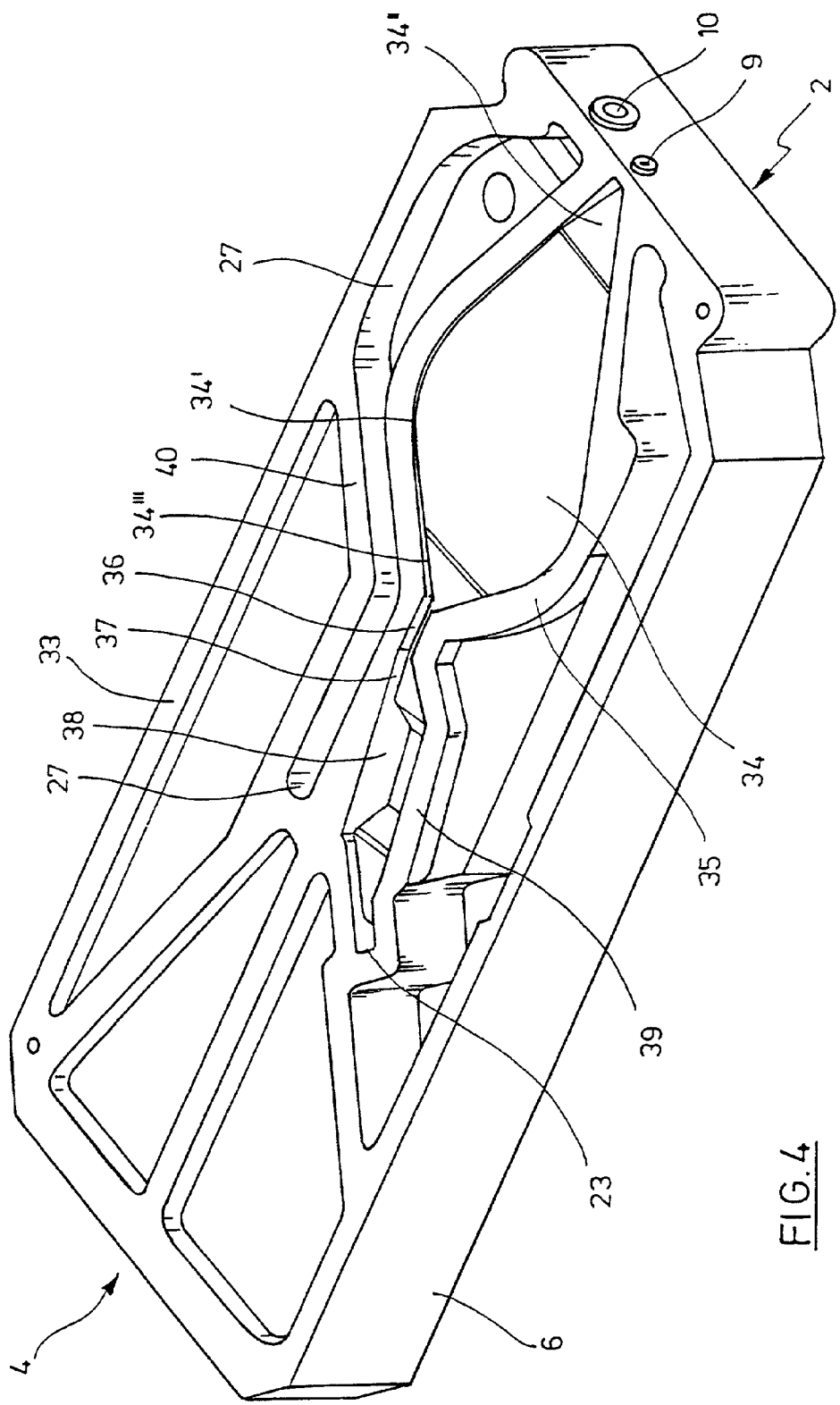
FIG. 4 shows the basic body of the same component in a perspective view onto the displacement side.

Furthermore, approximately at the centre of the basic body 6 in that area of the indentation 15' which is free from lamellar strips 18', a spigot 25 protrudes from the bottom 17' the outer end of which has an aeration port 26 which is connected to the mouth 10 via an aeration channel 27 passed through the spigot 25 and passed so to be open along the opposed side of the basic body 6 (cf. FIG. 4).

Figure 3:
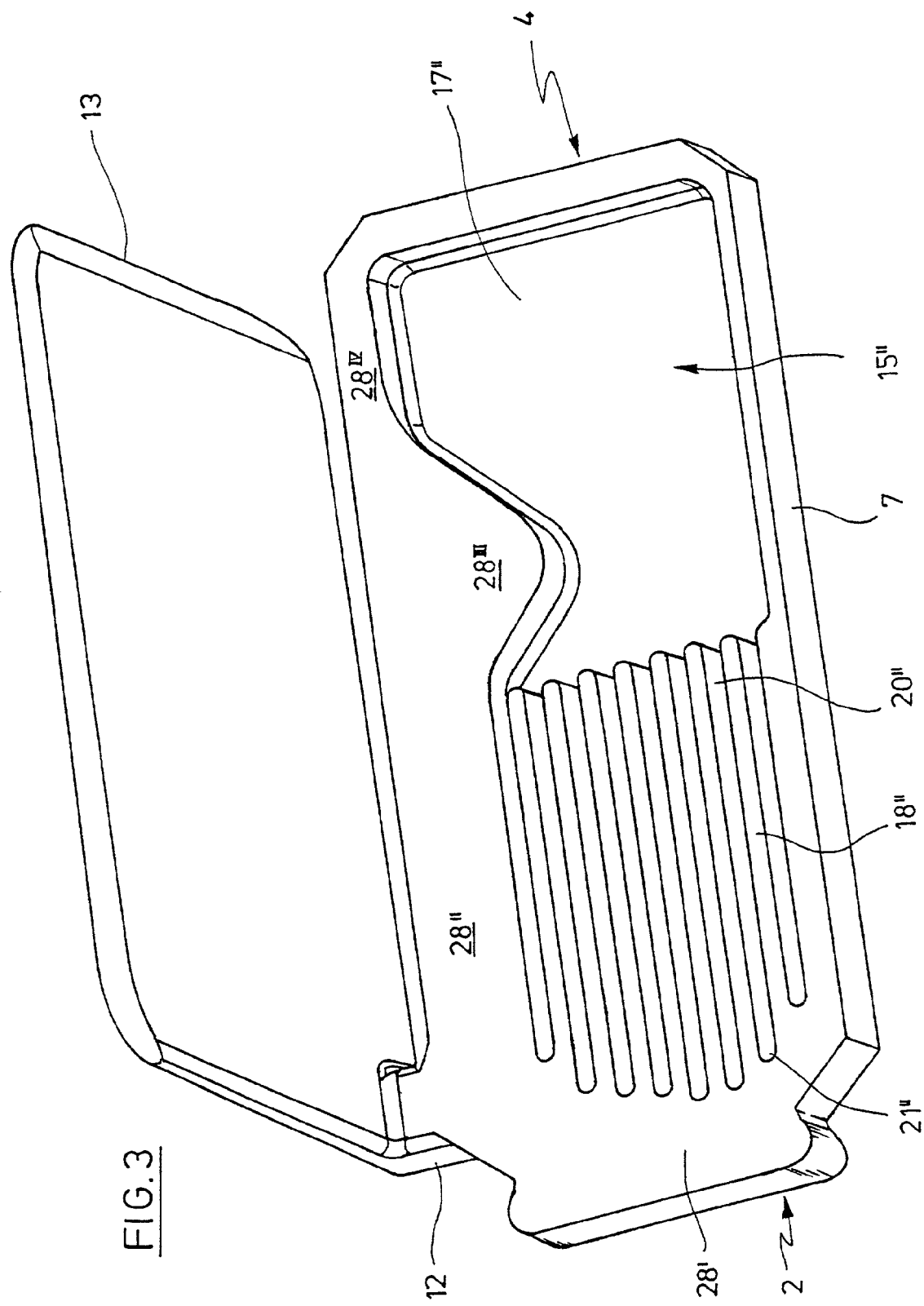
FIG. 3 shows the reservoir lid of the same component in a perspective view onto the inside.

Referring to FIG. 3, the reservoir lid 7 also has an indentation 15" which has a bottom 17" and is surrounded by a circumferential support surface 28. Lamellar strips 18" protrude from the bottom 17" and are oriented parallel in the longitudinal direction of the reservoir lid 7. The lamellar strips 18" extend from a widened region 28' of the support surface 28 that adjoins the end face 2. They extend approximately up to the middle of the length of the reservoir lid 7. They end at a distance from the bottom 17" at the level of the support surface 28. Capillary channels 20" extend between the lamellar strips 18" and next to the two outer lamellar strips 18" and are bordered by a shoulder 21" towards the end face 2 and are open towards the end face 4.

The support surface 28 has a widened portion 28" at a narrow side of the reservoir lid 7 in the area next to the lamellar strips 18". Adjacent thereto, it has a region 28''' which protrudes into that area of the indentation 15" which is free from lamellar strips. Adjacent thereto, it again has a narrower region $28^{IV}$.

The inscription flag 13 is integrally formed to the same narrow side of the reservoir lid 7 via the web 12.

Referring to FIG. 1, the basic body 6 and the reservoir lid 7 are placed upon each other and are connected to each other at their support surfaces 16, 28. The lamellar strips 18', 18" will then be flush wit each other as are the capillary channels 20', 20" therebetween. The capillary channels 20', 20" are interconnected by gap-shaped capillary connections 29 which are formed in the spaced are between the lamellar strips 18', 18" (cf. FIG. 10).

Figure 6:
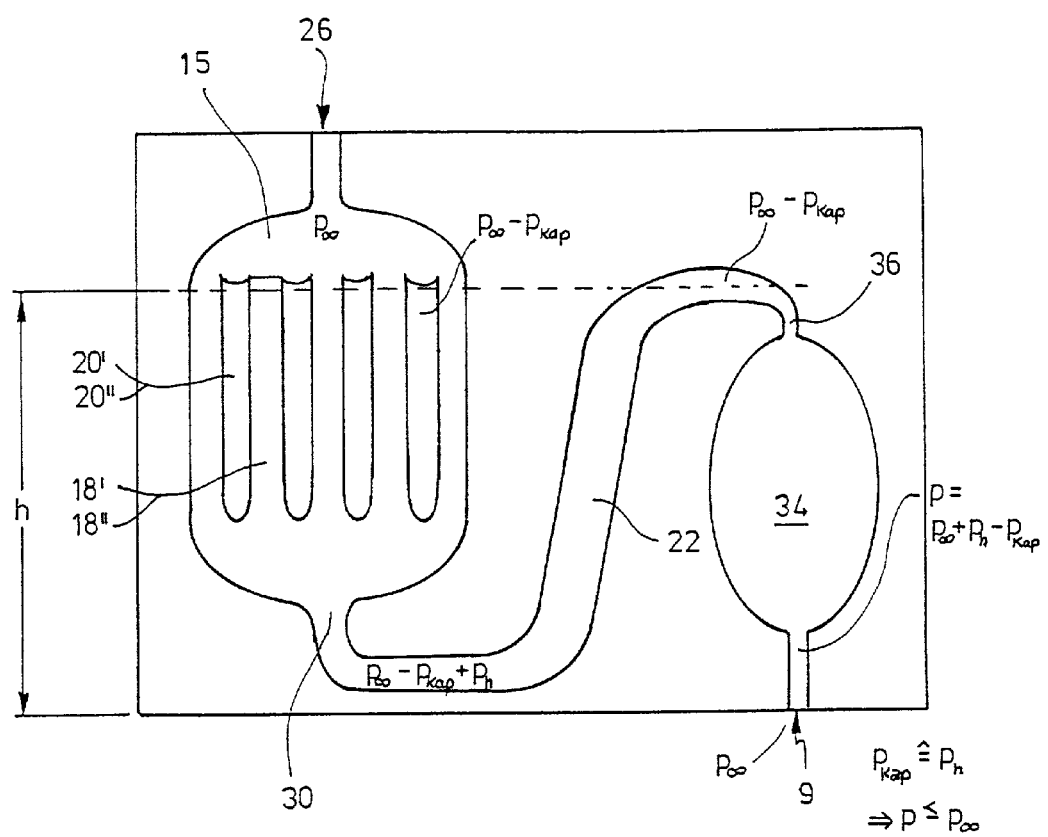
FIG. 6 shows the reservoir and the displacement chamber of the same component in a roughly schematic representation.

The first step portion 19 and that portion of the support surface 28' which protrudes inside from the support surface 16 define an outlet 30 of the reservoir 15 which contains the capillary channels 20', 20" and capillary connections 29 and is formed by the indentations 15', 15" (cf. FIG. 6). The capillary channels 20', 20" and capillary connections 29 open into the outlet 30 through an outlet port 30 with the outlet port 30 being formed between the shoulders 21', 21" (cf. FIG. 11).

Further, that portion of the support surfaces 28", 28''' which protrudes inside from the support surfaces 16, 16' defines the rising capillary channel 22. This one is open via a gap 31 formed towards the reservoir 15 between the support surfaces 28", 28''' and step portions 22', 22" the width of which gradually decreases towards the third step portion 22'''. The width of the gap 31 is constant in the area of the third step portion 22" (cf. FIG. 7).

Figure 7:
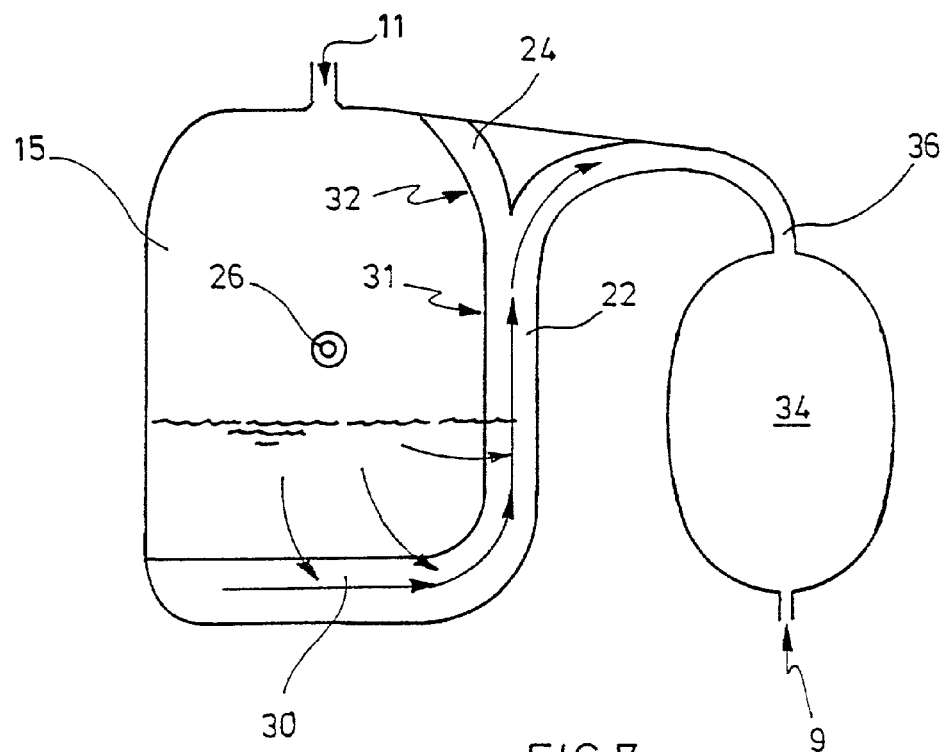
FIG. 7 shows the reservoir and the displacement chamber of the same component in the proportioning mode in a roughly schematic representation.

Further, that portion of the support surfaces 28''', $28_{IV}$ which protrudes beyond the support surfaces 16, 16' defines the filling channel 24 which also is open towards the reservoir 15 via a lateral gap 32 (cf. FIG. 7). The height of the gap 32 increases towards the end face wall 4.

Referring to FIG. 4, the basic body 6 has a circumferential support area 33 on the other large-surface side. This support surface has provided therein a displacement chamber 34 in the shape of an indentation which is defined by a drop-shaped wall 35 which ends at the same level as does the support area 33.

The displacement chamber 34 has a central portion 34' of a constant height and a bottom region 34" which heavily slopes with respect to the support area 33 and is connected to the proportioning outlet 9 at the lowest point. On the other side, the displacement chamber 34 also has a heavily sloping bottom region 34''' the lowest point of which is connected to an inlet 36 of the displacement chamber 34 that is formed as a throttle valve.

The passage 23 opens on this side of the basic body 6 into a connection channel 37 which is connected to the inlet 36 at the other end and has a prism-shaped indentation 38 in the central region.

The connection channel 37 is also bordered by an upstanding wall 39 which ends at the level of the support surface 33.

Likewise, the open portion of the aeration channel 27 is surrounded by a wall 40 which ends at the level of the support surface 33. The wall 40 partly coincides with the walls 35, 39.

On the same side, the basic body 6 further has more indentations which are intended to bring about an equalization of wall thicknesses.

Figure 5:
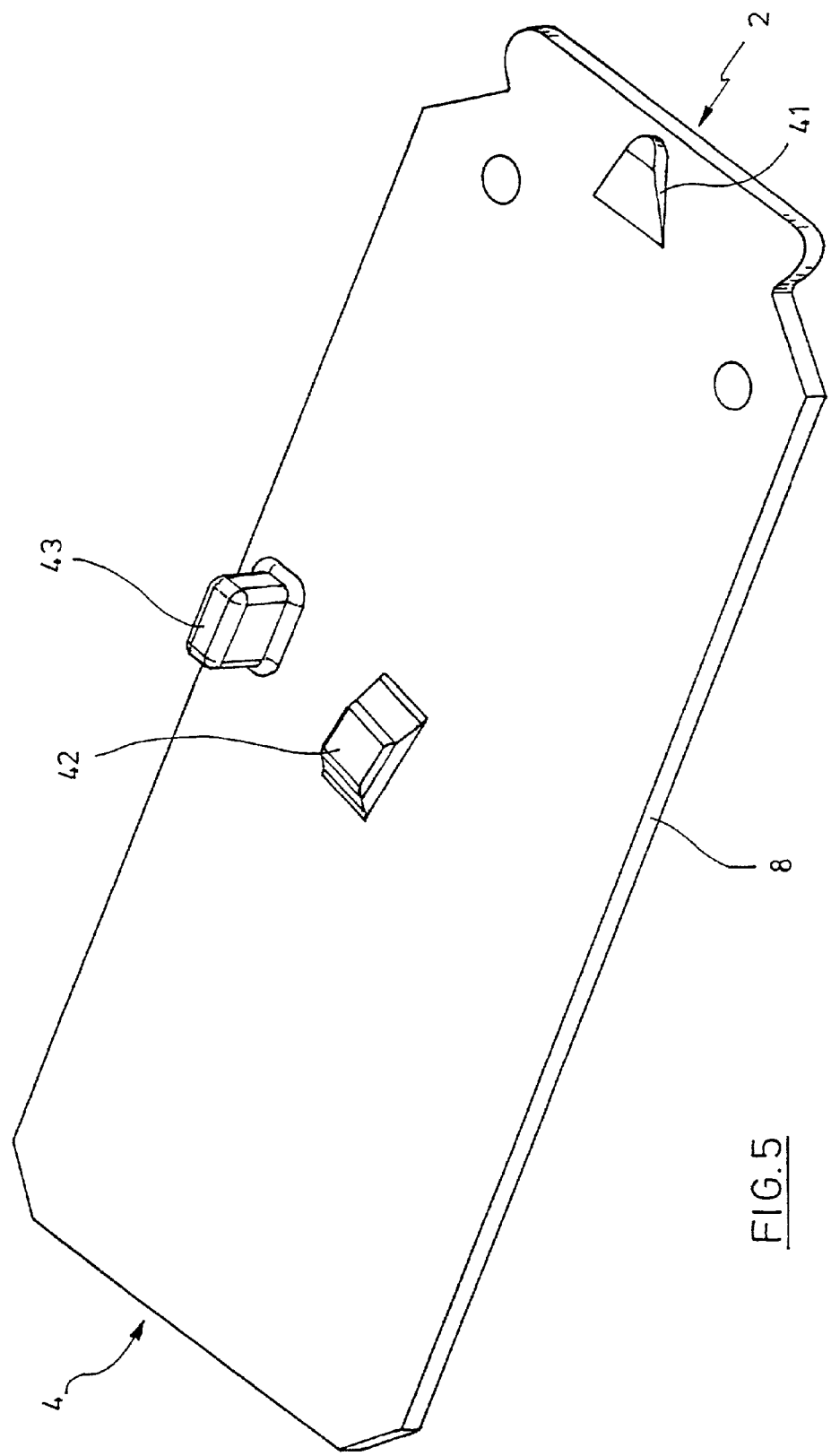
FIG. 5 shows the diaphragm lid of the same component in a perspective view onto the displacement side.

Referring to FIG. 5, the diaphragm lid 8 has an inside which substantially is planar. The lid has a ramp-shaped raised part 41. It includes a prism-shaped raised part 42 in a transparent area approximately in the centre. In addition, it has an injection-moulded spigot 43 close to the longitudinal side.

The diaphragm lid 8 is placed on the support surfaces 33, 35, 39, 40 of the basic body 6 and is connected with them. The ramp-shaped raised part 41 will engage the front-end region of the displacement chamber 34 here while simultaneously forming a front stop to position the diaphragm lid 8 on the basic body 6.

The prism-shaped raised part 42 engages the prism-shaped indentation 38 and the injection-moulded spigot 43 engages an adjoining indentation of the basic body 6.

Thus, the diaphragm lid 8 simultaneously defines a diaphragm-shaped cover of the displacement chamber 34. Moreover, it covers the connection channel 37 and the aeration channel 27.

The basic body 6, the reservoir lid 7, and the diaphragm lid 8 are made from plastic material by injection moulding. The plastic material concerned may particularly be polycarbonate. Blackened polycarbonate is used for the basic body 6 and polycarbonate which is transparent at least in part is used for the reservoir lid 7 and the diaphragm lid 8. This makes it possible to join the basic body 6, the reservoir lid 7, and the diaphragm lid 8 by laser welding. A laser beam penetrates through the transparent jointing component and is absorbed by the opaque jointing component here so as to produce a strong local heat-up and, hence, to cause the jointing components to be welded together. However, the jointing components may also be joined by an adhesive.

Proportioning the volumes as precisely as possible and forming and orienting the drop or jet of liquid requires that the proportioning outlet be accurately dimensioned. Particularly accurate dimensions can be achieved if the proportioning outlet is drilled or is structured by a laser (by imaging an intense laser beam on the workpiece through a mask).

The body 1 has the following dimensions in a realized sample:

Length=23.5 mm, width=10 mm, height=4.9 mm.

The inscription flag 13 has the following dimensions in the sample:

Length=19.5 mm, width=14.8 mm, height=abt. 1 mm.

The accumulating and proportioning component functions as follows:

The liquid to be proportioned is poured in through the filling port 11. This can be done by the manufacturer, particularly if the component is designed as a disposable, i.e. an expendable item. However, it is also possible to design the component as a re-usable item which can specifically be filled by the user or can be re-filled by the manufacturer.

For filling, the component is preferably oriented in a way that the liquid initially runs through the lateral gap 32 and into the filling channel 24 and causes the channel to fill the rising channel 22, the capillary channels 20', 20", and the capillary connections. As a result, air is gradually expelled out of the system and filling is ensured with no bubbles. The reservoir 15 is filled up to the upper edge of the lamellar strips 18', 18", as a maximum. Furthermore, the displacement chamber 34 is prefilled, with no bubbles occurring, via the passage 23 and the connection channel 37.

The filling port 11 is closed subsequently, e.g. by durably forcing in a glass sphere or introducing a removable stopper.

The liquid will not flow out by itself whatever the position of the component is because the hydrostatic pressure is very low in the proportioning outlet 9 and capillary forces are sufficient to retain the liquid in the system. This is illustrated by FIG. 6:

The outlet 30 at the bottom of the reservoir 15 is connected to the inlet 36 at the top of the displacement chamber 34 via the rising capillary channel 22. Reservoir 15 and displacement chamber 34 are approximately at the same level.

There is an ambient pressure $p_\infty$ in the aerated reservoir 15 above the lamellar strips 18', 18".

At the outlet 30 of the reservoir 15, the pressure in the liquid is reduced by the capillary pressure $p_{Kap}$ with respect to the ambient pressure and is increased by the hydrostatic pressure $p_h$ because of the height of the liquid column between the lamellar strips 18', 18".

Approximately the same pressure prevails in the proportioning outlet 9 which is located approximately at the level of the outlet 30 of the reservoir 15. There is an ambient pressure $p_\infty$ from outside at the proportioning outlet 9. Accordingly, no liquid will flow by itself out of the proportioning outlet if the capillary pressure $p_{Kap}$ is at least as high as is the hydrostatic pressure $p_h$. Since the hydrostatic pressure $p_h$ is low because the reservoir 15 and the displacement chamber 34 are arranged at the same level a relatively low capillary pressure $p_{Kap}$ is sufficient to retain the liquid in the system.

To proportion a liquid, the component is installed in a proportioning device so that the diaphragm lid 8 causes its region covering the displacement chamber 34 (preferably under a bias) to bear against an actor (e.g. a piezoelectric actor) of the proportioning device and a light barrier for the detection of bubbles of the proportioning device to be directed to the prism 42 of the diaphragm lid 8 from outside.

The component is releasably retained here by clamping it or snapping it into the proportioning device. The inscription field 13 externally bears on a casing wall of the proportioning device that engages the gap 14 so that the inscription is readable from outside. The proportioning device concerned may specifically be a hand-held device.

The actor is actuated for proportioning so that the diaphragm lid 8 partially is forced into the displacement chamber 34 and a defined liquid volume exits from the proportioning outlet in an open jet. The throttle valve in the inlet 36 of the displacement chamber 34 and the proportioning outlet 9 are adjusted to each other in a way that only a relatively small liquid volume is forced back into the reservoir 15 and most of the displaced liquid exits from the proportioning outlet 9. After pressure relief by the actor, the diaphragm lid 8 returns to its initial position because of its resiliency. The negative pressure in the displacement chamber 34 and the capillarity of the rising channel 22 cause fresh liquid to be fed into the displacement chamber 34 from the reservoir 15. The capillary pressure of the liquid in the proportioning outlet 9 prevents air from being drawn in through in the proportioning outlet 9.

During the proportioning operation, fresh liquid flows in through the outlet 30 of the reservoir 15 and the rising channel 22. The capillary pressure of the liquid acting into the lateral gap 31, 32 of the rising channel 22 and the filling channel 24 prevents air from being drawn in into the rising channel 22 from the reservoir 15. This is shown in FIG. 7.

Figure 8:
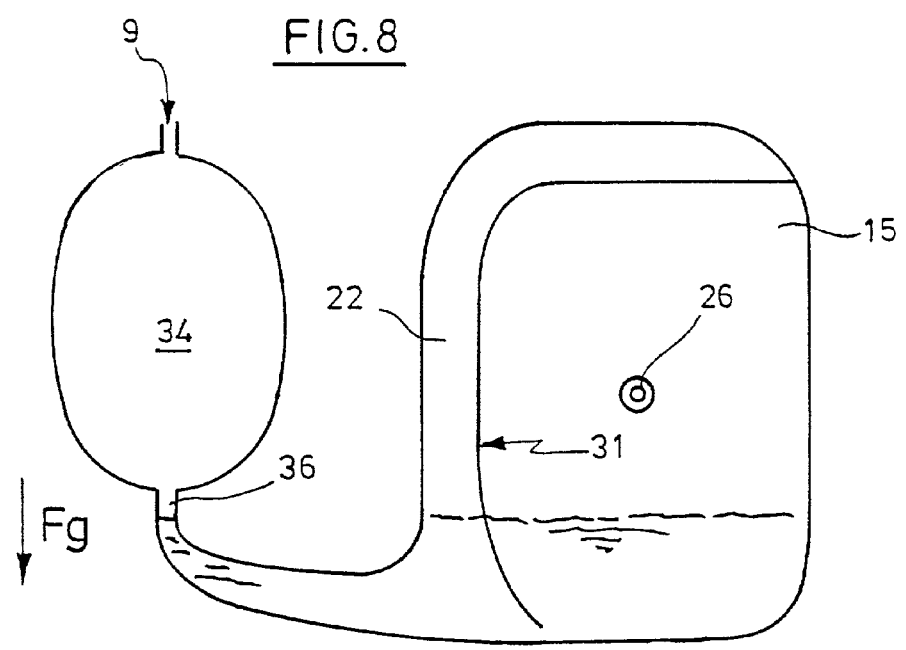
FIG. 8 shows the reservoir and the displacement chamber of the same component during centrifuging in a roughly schematic representation.

If bubbles should arise in the system notwithstanding this these may be removed from centrifuging. The orientation of the component in the centrifugal field $F_g$ is shown in FIG. 8. The liquid from the displacement chamber 34, the connection channel 37, the passage 23, and the rising channel 22 is collected in the upper region of the reservoir 15 through the lateral gap 31 of the rising channel 22. So is the liquid from the capillary region of the reservoir 15. Subsequently, the refilling of the system with no bubbles is possible in the way explained at the beginning of the description of operation.

In addition, FIGS. 7 and 8 illustrate that the liquid cannot enter the aeration port 26, no matter whether completely contained in the capillary cavities 20', 20", 29 or in that portion of the reservoir 15 which is free from it.

Figure 9:
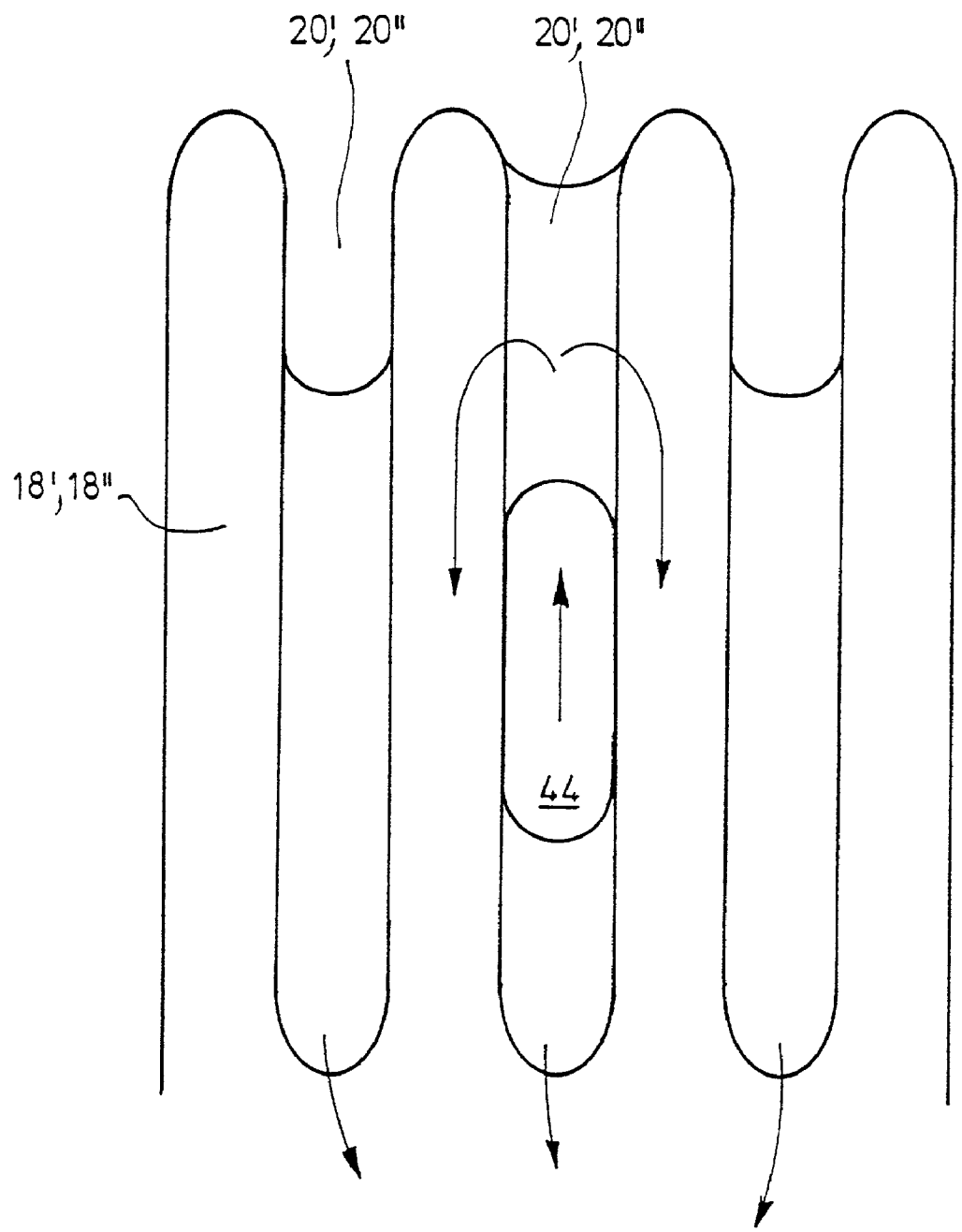
FIG. 9 shows the capillary structure of the reservoir of the same component in a roughly schematic longitudinal section.
Figure 10:
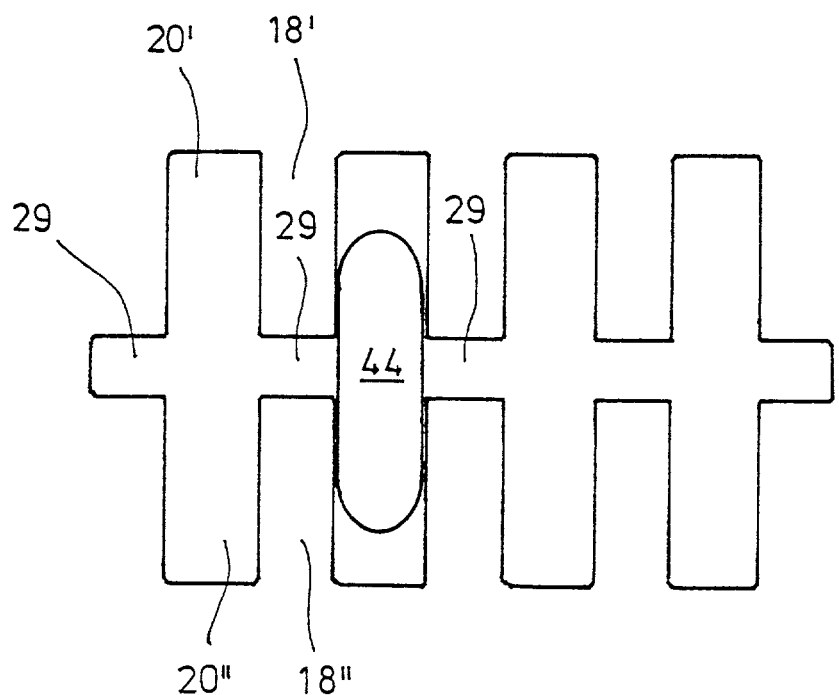
FIG. 10 shows the capillary structure of the reservoir of the same component in a roughly schematic cross-section.

In addition, the configuration of the capillary cavities 20', 20", 29 of the reservoir 15 counteracts annoying bubbles. As is shown in FIGS. 9 and 10 the formation of bubbles 44, e.g. because of heavy vibrations, is substantially limited to the capillary cavities 20', 20". A self-released gas removal is effected from the capillary cavities 20', 20" as the bubbles 44 move upwards between the lamellar strips 18', 18". As a result, liquid may escape into the capillary connections 29 and fill up the volumes occupied by the bubbles 44. The capillary connections 29 ensure that the outlet 30 is continuously supplied with liquid.

Figure 11:
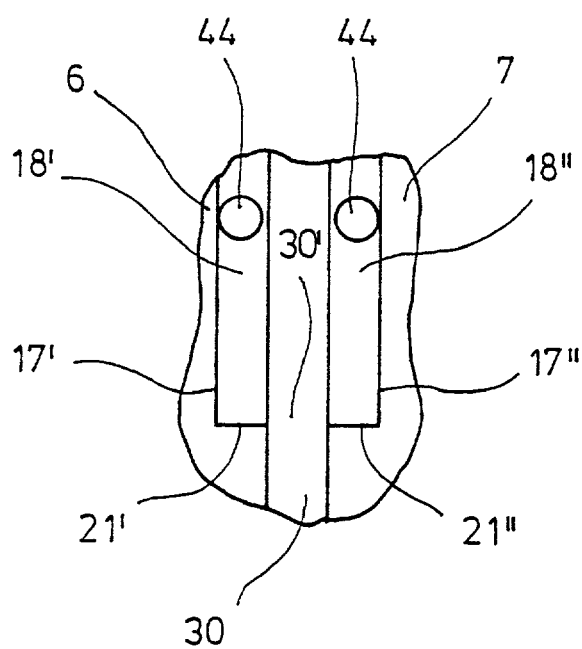
FIG. 11 shows the end portion of a capillary channel in a roughly schematic longitudinal section.

In addition, as is shown in FIG. 11 an entry of bubbles 44 into the outlet 30 of the reservoir 15 is prevented by the outlet ports 30' which occupy only some portion of the cross-section of the capillary channels 20', 20", and the propension of bubbles 44 to being deposited on a wall.

After use, the component may be removed from the proportioning device and may be discarded or refilled.

What is claimed is:

1. A microfluidic accumulating and proportioning component, comprising:
   a reservoir including an aeration port (26), and an outlet for a liquid and capillary cavities (20', 20");
   a displacement chamber (34) having an inlet (36) and a proportioning outlet (9) for the liquid, and a capillary channel (22) connecting the outlet (30) of the reservoir (15) with the inlet (36) of the displacement chamber (34), wherein in a position of the microfluidic component in which the proportioning outlet (9) is directed perpendicularly downward during proportioning, the displacement chamber (34) is disposed, at least partially, at a same level as the reservoir (15), the aeration port (26) is located at a top of the reservoir, the outlet (30) is located at a bottom of the reservoir (15), the inlet (36) of the displacement chamber (34) is located at a top of the displacement chamber (34) and the proportioning outlet (9) is located at a bottom of the displacement chamber, and wherein the microfluidic component further comprises a capillary gap (31) for connecting the capillary channel (22) with the reservoir (15) and extending laterally of the capillary channel (22), the capillary gap (31) enabling a rising liquid flow substantially from the outlet (30) of the reservoir (15) into the displacement chamber (34) through the capillary channel (22) in the proportioning mode and, when the component is disposed in a centrifugal field directed counter to the direction of the flow in the capillary channel (22) in the proportioning mode, a descending liquid flow from the displacement chamber (34) and the capillary channel (22) into the reservoir (15).

2. The component as claimed in claim 1 wherein the capillary gap (31) opens at least partially into a region of the reservoir (15) above the capillary cavities (20', 20").

3. The component as claimed in claim 1 wherein a capillarity of the capillary gap (31) is reduced from a bottom of the gap to a top thereof.

4. The component as claimed in claim 1 wherein the capillary cavities (20', 20") are formed as capillary channels leading to the outlet (30) of the reservoir (15).

5. The component as claimed in claim 1, wherein the capillary channel (22) is connected to the inlet (36) of the displacement chamber (34) via a connection duct (37) with which a filling level sensor is associated.

6. The component as claimed in claim 5, wherein the connection duct (37) is disposed between a highest level of the capillary channel (22) and the inlet (36) of the displacement chamber (34).

7. The component as claimed in claim 1, further comprising a filling port (11) at a top thereof that is connected to the reservoir (15).

8. The component as claimed in claim 7, wherein a filling channel (24) is disposed between the filling port (11) and the capillary channel (22).

* * * * *